US010022537B2

(12) United States Patent
Schüttler et al.

(10) Patent No.: US 10,022,537 B2
(45) Date of Patent: Jul. 17, 2018

(54) IMPLANTABLE NERVE ELECTRODE AND METHOD FOR PRODUCING AN IMPLANTABLE NERVE ELECTRODE

(71) Applicant: CorTec GmbH, Freiburg (DE)

(72) Inventors: Martin Schüttler, Freiburg (DE); Fabian Kohler, Freiburg (DE)

(73) Assignee: CorTec GmbH, Freiburg (DE)

( * ) Notice: Subject to any disclaimer, the term of this patent is extended or adjusted under 35 U.S.C. 154(b) by 0 days.

(21) Appl. No.: 14/152,558

(22) Filed: Jan. 10, 2014

(65) Prior Publication Data

US 2014/0128954 A1 May 8, 2014

Related U.S. Application Data

(63) Continuation of application No. PCT/EP2012/063463, filed on Jul. 10, 2012.

(30) Foreign Application Priority Data

Jul. 11, 2011 (DE) ........................ 10 2011 078 982

(51) Int. Cl.
*A61N 1/05* (2006.01)
*H01R 43/16* (2006.01)

(52) U.S. Cl.
CPC ......... *A61N 1/0551* (2013.01); *A61N 1/0553* (2013.01); *H01R 43/16* (2013.01); *Y10T 29/49224* (2015.01)

(58) Field of Classification Search
CPC ....................... Y10T 29/49224; A61N 1/0553; A61N 1/055; H01R 43/16
See application file for complete search history.

(56) References Cited

U.S. PATENT DOCUMENTS 4,010,756 A * 3/1977 DuMont .............. A61N 1/0587 606/129
5,987,361 A * 11/1999 Mortimer ............. A61N 1/0551 29/825

(Continued)

FOREIGN PATENT DOCUMENTS

DE 202010015346 U1 3/2011
WO 2009003182 A1 12/2008

OTHER PUBLICATIONS

Suaning G J et al, "Fabrication of multi-layer, high density micro-electrode arrays for neural stimulation and bio-signal recording", Neural Engineering, 2007, pp. 5-8, Piscataway, NJ, USA.

(Continued)

*Primary Examiner* — Alyssa M Alter
(74) *Attorney, Agent, or Firm* — Myers Wolin, LLC

(57) ABSTRACT

The invention relates to an implantable nerve electrode (1) that comprises an electrically insulating substrate (2) with conductor traces (3) running therein, electrode contacts (4) and connection contacts (5), wherein the conductor traces (3) connect the electrode contacts (4) to the connection contacts (5), and wherein the electrode contacts (4) can be connected to the nerves of a nervous system, each of the conductor traces (3) having an at least partial sheathing (13) made of a polymer that is mechanically strong and a good insulator. The invention further relates to a method for producing an implantable nerve electrode (1).

3 Claims, 3 Drawing Sheets

(56) References Cited

U.S. PATENT DOCUMENTS

Figure 1:
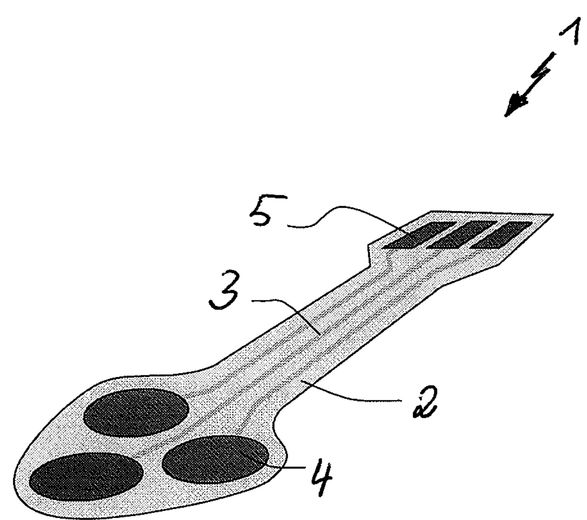

| | | | | |
|---|---|---|---|---|
| 2007/0128420 | A1 | 6/2007 | Maghribi | |
| 2008/0027524 | A1 * | 1/2008 | Maschino | A61N 1/0551 607/118 |
| 2009/0254162 | A1 * | 10/2009 | Quinci | A61N 1/05 607/115 |
| 2011/0034977 | A1 | 2/2011 | Janik et al. | |
| 2011/0071596 | A1 | 3/2011 | Kara | |

OTHER PUBLICATIONS

International Search Report for Corresponding PCT Application No. PCT/EP2012/063436, dated Oct. 17, 2012.

Henle et al., "First long term in vivo study on subdurally implanted Micro-ECoG electrodes, manufactured with a novel laser technology", Biomed Microdevices (2011), vol. 13, pp. 59-68, Springer Science+Business Media, LLC, Sep. 14, 2010.

Hassler et al., "Polymers for Neural Implants", Journal of Polymer Science: Part B: Polymer Physics, vol. 49, pp. 18-33, Wiley Online Library, Wiley Periodicals, Inc., Aug. 20, 2010.

International Preliminary Report on Patentability with the Written Opinion issued for corresponding International Patent Application No. PCT/EP2012/063463 dated Jan. 14, 2014.

Teng-Hui, "The Research of the Neuro-Stimulating Microelectrodes for Visual Prosthesis", Thesis for Master of Shanghai Jiao Tong University, Shanghai Jiao Tong University, Shanghai, China, Jan. 2008, with English abstract and partial English translation.

Min et al., "New Fabrication of Retina Electrodes by Micro-Patterning of PI", Research Institute of Micro/Nano Science and Technology, Shanghai Jiao Tong University, Shanghai, China, Feb. 2010, with English abstract and partial English translation.

Chinese Search Report issued for corresponding Chinese Patent Application No. 201280034503X dated Dec. 8, 2014 with a partial English translation.

German Search Report issued for corresponding German Patent Application No. 10 2011 078 982.0 dated May 9, 2012 with a partial English translation.

* cited by examiner

IMPLANTABLE NERVE ELECTRODE AND METHOD FOR PRODUCING AN IMPLANTABLE NERVE ELECTRODE

CROSS REFERENCE TO RELATED APPLICATIONS

The present application is a continuation of International Application No. PCT/EP2012/063463, filed on Jul. 10, 2012, which claims priority to German Application No. 102011078982.0, filed Jul. 11, 2011, the contents of which are incorporated herein by reference.

FIELD OF THE INVENTION

The invention relates to an implantable nerve electrode according to the preamble of claim 1 as well as to a method for producing such an implantable nerve electrode.

BACKGROUND

Functional electrical stimulation restores for many patients having implanted devices, as for example, pacemakers, defibrillators, bladder stimulators, implants for coping with pain, tremor, epilepsy and for recovering the sense of hearing, body functions which have been lost. For this, implantable nerve electrodes are applied.

In prior art, it is known to produce implantable nerve electrodes by means of laser treatment from medical silicone and a metal foil. The basis of the known process is the separation of conductive paths and contact areas from a metal foil typically 5 to 25 μm thin by means of a laser. The conductive path, electrode and contact areas are embedded into medical silicone, whereby the single signal paths may be isolated electrically from each other. The contact areas subsequently are exposed by means of the laser.

This known technology, however, has two problems: The conductive paths are extremely fragile due to their fineness. The elastic silicone may only protect them to a very limited extend from mechanical influences, as, for example, while handling during the implantation. Accordingly, laser processed nerve electrodes, on the one hand, are relatively prone to breakage of conductive paths. On the other hand, silicone has a low electric strength. When a stimulation is carried out by means of nerve electrodes electrically, voltages of several 10V between two adjacent conductive paths may occur. According to manufacturer specifications, the electric strength of silicone may be lowered to 2 kV/mm by storing it in water. A voltage of 20 V between two adjacent conductive paths with a distance of 10 μm, thus, may lead to an electrical break down. This fact limits the integration density of the electrode.

In order to solve the problem of the inadequate stability, it is known in prior art to, for example, arrange the conductive paths in meandering lines. Hereby, a certain extensibility of the conductive paths is achieved. However, the increased space requirement is disadvantageous for the meandering arrangement of conductive paths, which in turn has a negative impact on the maximum integration density.

A further approach involves the embedding of conductive paths in thicker and harder silicone. However, also this variant has little success, because also thicker silicone is much more elastic than the metal embedded therein. The occurring mechanical forces further influence the conductive paths substantially, and lead to their damage.

It also has been attempted to increase the mechanical stability by adding a polymer foil which is mechanically very strong and a further silicone layer, which have been inserted into the multi-layer structure of silicone-metal-silicone. Hereby, an improvement of the mechanical stability of the nerve electrode may, however, be achieved, but the new multi-layer structure silicone-metal-silicone-polymer-foil-silicone is unfavorable in that the layer of the rigid polymer foil which is non-compressible or non-extendable defines the mechanically neutral fiber within the multi-layer structure. With strong bending movements, therefore, compressional or tensile forces of the metal conductive paths occur.

With respect to the second problem of the low electrical strength of the silicone in which the conductive paths are embedded, up to now no approach to a solution has been found.

Therefore, it is an object of the present invention to provide an implantable nerve electrode and a method for producing a nerve electrode according to which an effective protection for the conductive paths and at the same time a high integration density may be achieved.

SUMMARY

This object is solved by an implantable nerve electrode having the features according to claim 1, and by a method for producing a nerve electrode having the features according to claim 10. Preferred embodiments of the invention are specified in the respective dependent claims.

According to the invention, an implantable nerve electrode is provided having an electrically insulating substrate with conductive paths running therein, electrode contacts and terminal contacts, wherein the conductive paths connect the electrode contacts to the terminal contacts, and wherein the electrode contacts are connectable to nerves of a nervous system, wherein each of the conductive paths has an at least partial jacket made from a mechanically rigid and electrically well insulating polymer. Because each conductive path within the composite silicone-metal-silicone is sheathed individually by a mechanically rigid and electrically well insulating polymer at least partially, on one hand, the disadvantages with respect to the insufficient mechanical stability of the conductive paths may be overcome. On the other hand, a high integration density can be achieved, because the jacket insures a good electrical insulation. By means of the configuration according to the invention, the mechanically neutral fiber lies within the plane of the metal, whereby also with high bending loads, no compression or extension of the conductive paths occurs. For a patient, whom a nerve electrode will be implanted, by the high mechanical stability, a higher reliability of the implant can be secured. Also, the electrical insulation between the single conductive paths of the nerve electrode allows a further miniaturization of the structure to be introduced into the body of the patient, as well as also the implementation of complex systems with high integration density.

According to a preferred embodiment, the mechanical rigid and electrically well insulating polymer from which the jacket is made, comprises parylene, in particular parylene C, polyethylene or polypropylene. These materials have an electrical strength 100 times higher than a silicone which has been used up to now. In particular, parylene C has an electrical strength of 220 kV/mm, allowing a substantially improved integration density of the conductive paths.

According to a further preferred embodiment, the conductive paths, the electrode contacts and the terminal contacts are made from a laser structured metal foil. The production of the conductive paths, electrode and terminal contacts by means of laser enables a specifically well reproducibility and a high degree of automation.

It is especially preferred, when each single conductive path has an individual jacket. This configuration offers a specifically effective protection of the fragile conductive paths.

Preferably, each of the conductive paths is covered completely by a jacket, which even further enhances the protection of the conductive paths.

According to a further preferred embodiment, the mechanically rigid and electrically well insulating polymer is present additionally between the conductive paths. Hereby, a mechanical enforcement of the nerve electrode may be implemented specifically locally.

Preferably, the conductive paths being sheathed by the mechanical rigid and electrically well insulating polymer are embedded in silicone, in particular, in medical silicone, in particular, polydimethylsiloxan, which forms the electrically insulating substrate of the implantable nerve electrode.

According to a further preferred embodiment, the jackets made from the mechanically rigid and electrically well insulating polymer are connected to each other, in order to form the electrically insulating substrate of the implantable nerve electrode. With this it is advantageous that further layers, the silicone layers, may be omitted. The production method of such a nerve electrode, thereby, is simplified accordingly, and thus, is cheaper.

Moreover, it is advantageous, if the conductive paths, the electrode contacts, and the terminal contacts are made from stainless steel or from platinum.

According to the invention, a method for producing an implantable nerve electrode is provided, whereby the method comprises the following steps: Providing a mechanical support: Applying a non-stick coating to the upper surface of the mechanical support (if necessary), applying a first silicone layer onto the upper surface of the mechanical support, laminating a metal foil being coated on one side with the first layer of a mechanically rigid and electrically well insulating polymer, wherein the coated side of the metal foil faces the first silicone layer, structuring the metal foil by means of laser in order to expose conductive paths, electrode contacts and terminal contacts, applying a cover layer made from the mechanically rigid and electrically well insulating polymer onto the structured metal foil, wherein the cover layer connects to the first layer made from a mechanically rigid and electrically well insulating polymer. By means of the inventive method, the advantages described above are achieved. In particular, hereby a nerve electrode having an improved mechanical stability and a higher integration density of the conductive paths may be produced. The inventive production process, moreover, enables a locally definable and, if needed, an isotropic rigidity of the nerve electrode, which may be adapted to the respective application.

According to a preferred embodiment, the method further comprises the step of structuring the cover layer by means of laser.

According to a further preferred embodiment, the method further comprises the step of applying a second silicone layer, in particular, thin-coating of the liquid silicone onto the structured cover layer.

According to still a further preferred embodiment, the method further comprises the step of curing the second silicone layer.

Preferably, the method further comprises the step of exposing the electrode contacts and the terminal contacts by means of laser.

According to a further preferred embodiment, the method further comprises the step of defining the outer contours of the implantable nerve electrode by means of laser.

Preferably, the method further comprises the step of separating by means of laser the defined implantable nerve electrode from the support.

According to a further preferred embodiment, the non-stick coating comprises a PVC foil, in particular, Tesafilm.

BRIEF DESCRIPTION OF THE PREFERRED EMBODIMENTS

Figure 2:
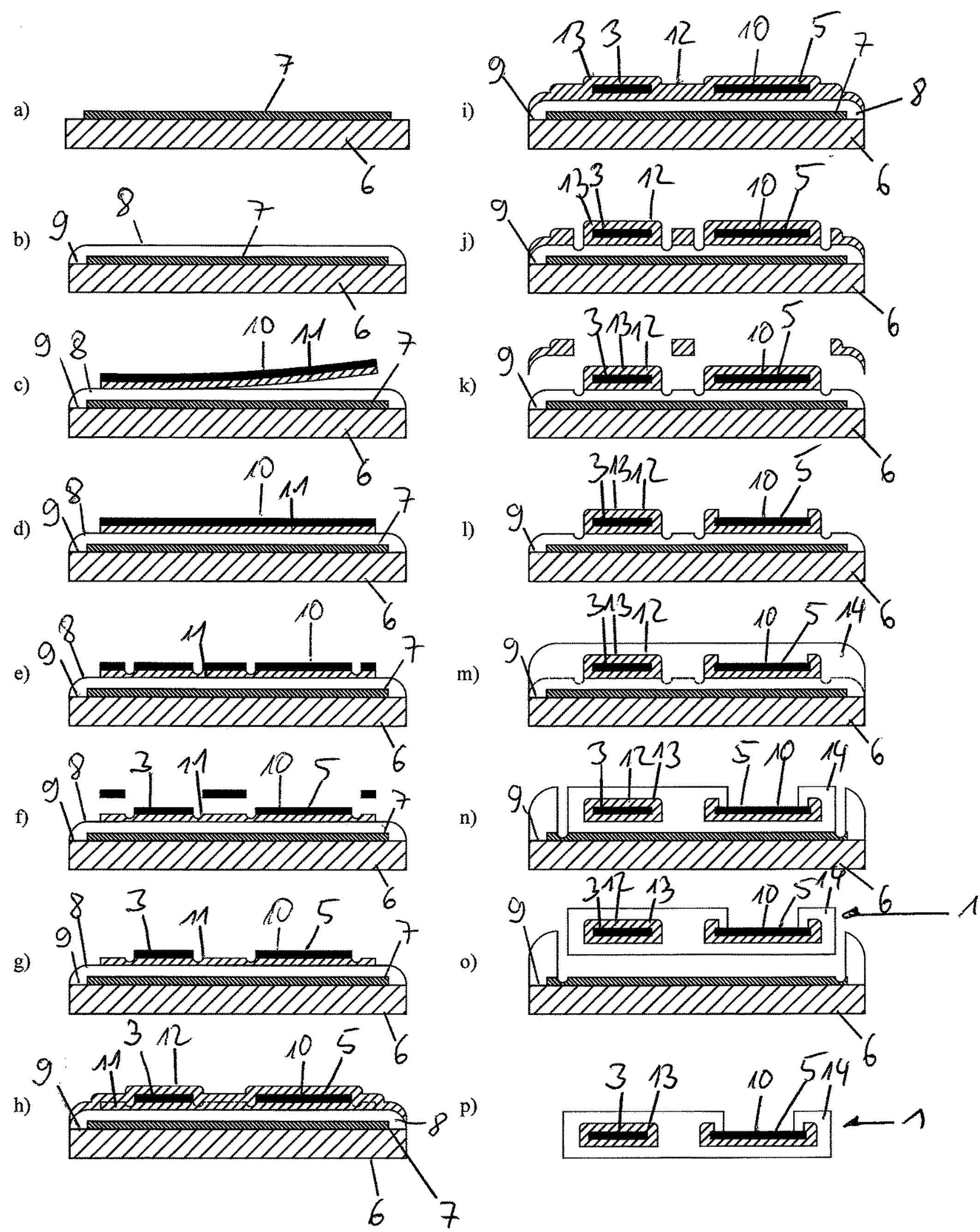
Figure 3:
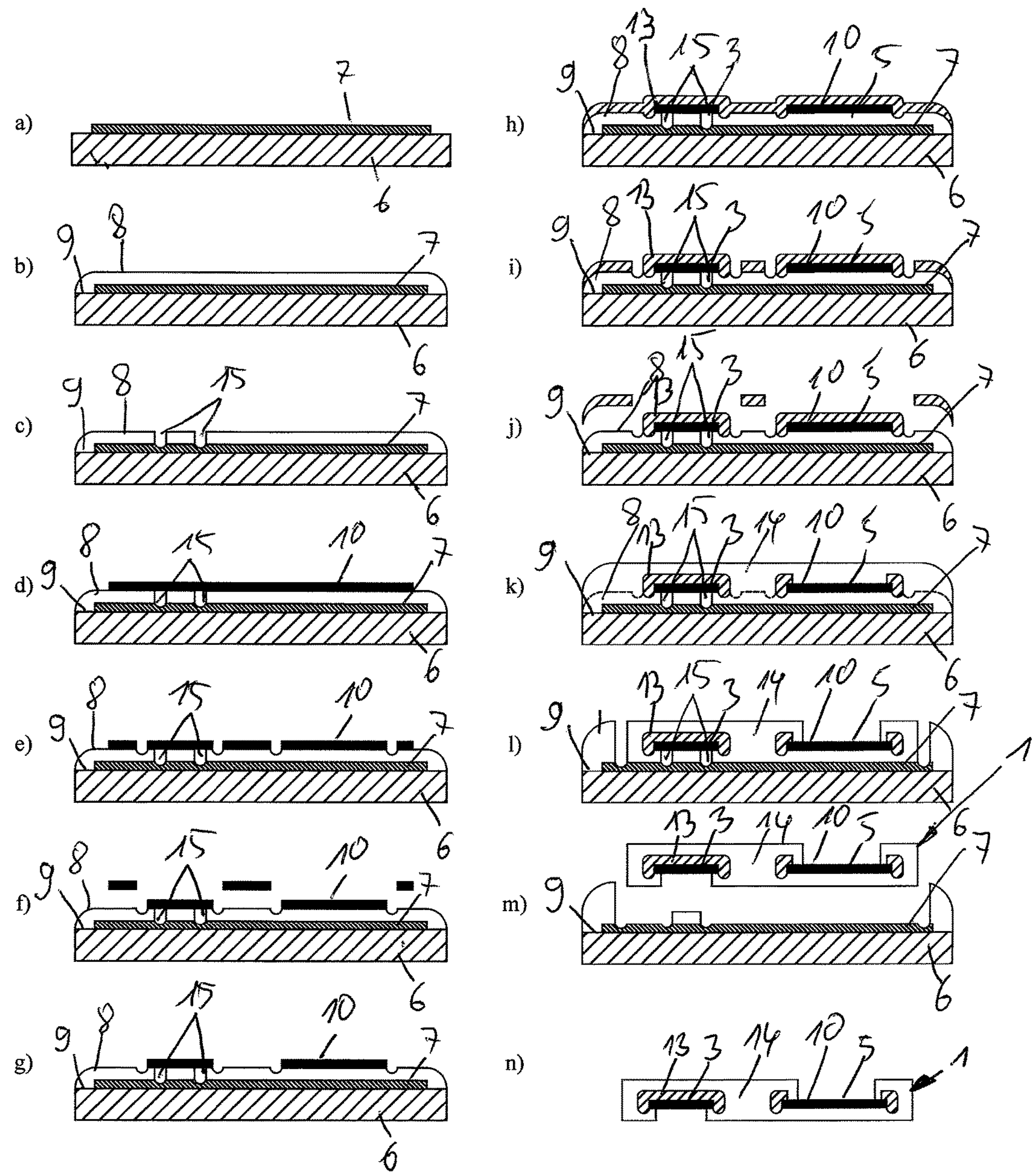

In the following, embodiments of the invention will be further described with reference to the accompanying drawings, in which:

FIG. 1 is a perspective view of an implantable nerve electrode according to prior art;

FIGS. 2*a* to 2*p* are respective sectional views of a sequence of method steps of a method for producing an implantable nerve electrode according to an embodiment of the invention; and FIGS. 3*a* to 3*n* are respective sectional views of the sequence of method steps of a method for producing an implantable nerve electrode according to a further embodiment of the invention.

DETAILED DESCRIPTION OF THE PREFERRED EMBODIMENTS

FIG. 1 is a perspective view of an implantable nerve electrode 1 according to prior art. The nerve electrode 1 comprises an electrically insulating substrate 2, which here is medical silicone, into which the conductive paths 3 are embedded. The conductive paths 3 connect electrode contacts 4 to terminal contacts 5.

FIGS. 2*a* to 2*p* are respective sectional views of the sequence of method steps of a method for producing an implantable nerve electrode according to an embodiment. In FIG. 2*a*, the first method step is illustrated, in which a non-stick coating 7, as e.g., self-adhesive PVC foil, as for example, Tesafilm, is applied onto a mechanical support 6, which for example consists of glass or ceramics. In the second step, illustrated in FIG. 2*b*, a first silicone layer 8 of liquid silicone being only a few 10 μm thin is spin-coated onto the upper surface 9 of the support 6 which is already provided with the non-stick coating 7, and is cured subsequently. Thereafter, as shown in FIGS. 2*c* and 2*d*, a metal foil 10, which in the embodiment has a thickness of 12.5 μm and is made from platinum, and which is provided on one side with a first layer 11 from a mechanically rigid and electrically well insulating polymer being only a few μm thick, in the embodiment parylene C, is laminated onto the first silicone layer 8. In the subsequent step, which is illustrated in FIG. 2*e*, the metal foil 10 is structured by means of a laser such that a metal, which later on will not serve as conductive paths 3, electrode or terminal contacts (4, 5; see FIG. 1) may be removed, as is visible in FIGS. 2*f* and 2*g*. Then, as is illustrated in FIG. 2*h*, the cover layer 12 being only a few μm thick and also consisting of parylene C, is applied which connects to the first layer 11 (FIG. 2*i*), and for each conductive path 3, an individual jacket 13 is formed. In the next step, which is illustrated in FIG. 2*j*, the external contours of the subsequent parylene layer, namely, the cover layer 12 are structured with a laser and the excessive parylene is removed (FIG. 2*k*). In a further laser step, which is illustrated in FIG. 2*l*, the cover layer 12 is removed at the locations of the subsequent electrodes, illustrated here is the terminal electrode 5. By spin-coating of a second silicone layer 14, which only is a few µm thick, and subsequent curing, the conductive paths 3 sheathed with parylene are completely embedded in silicone. By means of a laser, then the openings for electrode and terminal contacts, illustrated here is the terminal contact 4, are cut into the silicone (FIG. 2*n*), and the external contours of the nerve electrode 1 are defined. Due to the poor adhesion between silicone and the non-stick coating 7, now the nerve electrode 1 may be separated from the mechanical support 6, as is visible in FIG. 2*o*. In FIG. 2*p*, eventually, the nerve electrode 1, which is produced at the end of the production procedure, is shown.

However, according to a further embodiment it is also possible to omit a coating with a second silicone layer 14. Then, hereby, the method steps shown in FIGS. 2*i* and 2*j* are carried out such that all conductive paths 3 are mechanically connected to each other via their jackets 13 from parylene C, and only the external contour of the nerve electrode is defined into the polymer by means of laser cuts. According to the method step shown in FIG. 2*l*, then the electrode and terminal contacts are exposed by means of laser, and a finished nerve electrode 1 may be pulled off from the first silicone layer 8. The nerve electrode 1, thus produced, has according to this production procedure conductive paths 3 and electrode and terminal contacts 4, 5, which are embedded into a substrate from parylene C.

FIGS. 3*a* to 3*n* are respective sectional views of the sequence of method steps of a method for producing an implantable nerve electrode 1 according to a further embodiment according to which the conductive paths 3 are only partially covered with a mechanically rigid and electrically well insulating polymer, here also parylene C. By this, a simplification of the production method is achieved, and it is enabled to implement an electrical opening "downwards" as will be obvious in the following. The method steps illustrated in FIGS. 3*a* and 3*b* correspond to the ones in FIGS. 2*a* and 2*b*, and therefore, will not be repeatedly described. In the step illustrated in FIG. 3*c*, the edges of the subsequent electrode openings are processed by means of laser, as is shown by reference numeral 15. Then, as shown in FIG. 3*d*, a metal foil 10 is laminated onto the first silicone layer 8, which subsequently is cut by means of a laser, such that the areas not required as conductive paths 3, electrode or terminal contacts 4, 5 (see FIG. 1) are removed (FIGS. 3*e*, 3*f*, 3*g*). Subsequently, parylene C is applied to the surface in a planar manner to form a partial jacket 13 for the conductive paths 5 (FIG. 3*h*). In FIG. 3*e*, the next step is illustrated, in which the layer from parylene C is structured by means of laser such that undesirably coated areas subsequently may be freed from parylene C (FIG. 3*j*). Subsequently, a silicone layer 14 is applied (FIG. 3*k*), which is cured and then is processed such that (FIG. 3*l*) electrode and terminal contacts facing "upwards", here the terminal contact 5, are exposed and the external edge of the nerve electrode 1 is defined. For completion of the production method, the mechanical support 6 is removed (FIG. 3*m*) such that the finished nerve electrode 1 is obtained (FIG. 3*n*).

LIST OF REFERENCE NUMERALS

1 nerve electrode
2 electrically insulating substrate
3 conductive path
4 electrode contact
5 terminal contact
6 support
7 non-stick coating
8 first silicone layer
9 upper surface of the support
10 metal foil
11 first layer
12 cover layer
13 jacket
14 second silicone layer
15 edge

What is claimed is:

1. An implantable nerve electrode, comprising:

an electrically insulating substrate with a plurality of conductive paths running therein, electrode contacts, and terminal contacts, the plurality of conductive paths connecting the electrode contacts to the terminal contacts, and the electrode contacts configured to connect to nerves of a nervous system, each single one conductive path of the plurality of conductive paths having an individual, at least partial jacket from a mechanically rigid and electrically well insulating polymer which is applied in a planar manner, each conductive path with its individual, at least partial jacket being embedded in silicone which forms the electrically insulating substrate, each jacket being separated from each other jacket by silicone, wherein the polymer comprises one of parylene, parylene C, polyethylene, and polypropylene, and wherein the plurality of conductive paths, the electrode contacts, and the terminal contacts are made from a laser structured metal foil.

2. The implantable nerve electrode of claim 1, wherein each of the plurality of conductive paths is covered completely by its jacket.

3. The implantable nerve electrode of claim 1, wherein the plurality of conductive paths (3), electrode contacts (4), and terminal contacts (5) are made from metal, in particular, from stainless steel or from platinum.

* * * * *